(12) United States Patent
Sengupta et al.

(10) Patent No.: US 8,620,458 B1
(45) Date of Patent: Dec. 31, 2013

(54) ACTIVE FIXATION MEDICAL LEAD AND RELATED METHOD AND SYSTEM

(75) Inventors: Shimul Sengupta, Chatsworth, CA (US); Yougandh Chitre, Santa Clara, CA (US); Cheuk Tang, Pasadena, CA (US)

(73) Assignee: Pacestter, Inc., Sylmar, CA (US)

( * ) Notice: Subject to any disclaimer, the term of this patent is extended or adjusted under 35 U.S.C. 154(b) by 248 days.

(21) Appl. No.: 13/166,716

(22) Filed: Jun. 22, 2011

Related U.S. Application Data (63) Continuation of application No. 11/748,915, filed on May 15, 2007, now Pat. No. 7,991,484.

(51) Int. Cl.
*A61N 1/37* (2006.01)

(52) U.S. Cl.
USPC ............................ 607/127; 607/126; 607/116

(58) Field of Classification Search
USPC ........................................ 607/116–130, 10, 3
See application file for complete search history.

(56) References Cited

U.S. PATENT DOCUMENTS

| | | | |
|---|---|---|---|
| 4,402,323 A | 9/1983 | White | |
| 6,567,704 B2 | 5/2003 | Sundquist et al. | |
| 6,609,027 B2 | 8/2003 | Kroll et al. | |
| 6,687,550 B1 | 2/2004 | Doan | |
| 7,305,270 B1 * | 12/2007 | Kroll et al. | 607/127 |
| 2002/0077685 A1 | 6/2002 | Sundquist et al. | |
| 2005/0004611 A1 | 1/2005 | Edwards et al. | |

FOREIGN PATENT DOCUMENTS

WO    WO02/081022    10/2002

* cited by examiner

*Primary Examiner* — Carl H Layno
*Assistant Examiner* — Paula J Stice (57) ABSTRACT

An implantable medical lead of the invention comprises an electrically active helix electrode extendable and retractable relative to a distal tip of the lead, an electrically conductive mapping collar disposed at the lead's distal tip and a proximal end carrying an electrical connector assembly. The electrical connector assembly comprises a first terminal connected to the helix electrode and a second terminal separately connected to the mapping collar. An advantage of the independent helix electrode and mapping collar circuits is that the implanting physician can confirm from separate electrode impedance readings that the helix is in fact extended and fully embedded within the myocardium. Further, the independent mapping collar and helix electrode circuits may be used, in conjunction with a configurable or programmable switch network, to provide the implanting physician with a choice of electrode impedances.

5 Claims, 8 Drawing Sheets

ACTIVE FIXATION MEDICAL LEAD AND RELATED METHOD AND SYSTEM

CROSS REFERENCE TO RELATED APPLICATIONS

This application is a continuation of U.S. patent application Ser. No. 11/748,915, filed May 15, 2007 now U.S. Pat. No. 7,991,484, titled "Active Fixation Medical Lead and Related Method and System."

FIELD OF THE INVENTION

The present invention relates generally to implantable medical devices, and particularly to (i) an improved active fixation or screw-in type pacing lead, (ii) a method for electrically determining in vivo whether such lead has been properly positioned relative to body tissue such as the endocardium, and (iii) a system incorporating such a lead, wherein the lead's electrode impedance may be selected in accordance with the preferences of the implanting physician.

BACKGROUND OF THE INVENTION

Body implantable electrical leads form the electrical connection between a pulse generator, such as a cardiac implantable medical device (IMD), and body tissue, such as the endocardium, which is to be electrically stimulated. As is well known, the leads connecting IMDs with the heart may be used for pacing or for sensing electrical signals produced by the heart, or for both pacing and sensing in which case a single lead serves as a bidirectional pulse transmission link between the IMD and the heart. An endocardial type lead, that is, a lead which is inserted into a vein and guided therethrough into a cavity of the heart, typically includes at its distal tip an electrode designed to contact the endocardium, the tissue lining the inside of the heart. The lead further includes a proximal end carrying an electrical connector assembly adapted to be received by a receptacle in the IMD. A flexible cable or coil conductor surrounded by an insulating sheath couples an electrical terminal on the electrical connector assembly with the electrode at the distal tip. For bipolar stimulation and/or sensing, a similar connection may be provided for a ring electrode disposed proximal of the tip electrode.

To prevent displacement or dislodgement of the tip electrode and to maintain the necessary stable electrical contact between the tip electrode and the body tissue, the electrode must be firmly anchored relative to the tissue. For example, an electrode-carrying, distal end portion of a lead body may be configured to bias an electrode into engagement with the target body tissue such as that of a vessel in the coronary sinus region of the heart and thereby passively fix the electrode's position. Another passive fixation mechanism makes use of tines or nubs projecting from the distal end portion of the lead body. Such projections engage the trabeculae within a chamber of the heart or the wall of a vessel receiving the lead.

Another type of lead, sometimes referred to as an active fixation lead, typically includes a pointed, helical element extendable and retractable relative to the lead's tip and thereby adapted to be screwed into the cardiac tissue, typically the endocardium, to be stimulated. In this fashion, the position of the electrode-carrying distal end portion of the lead body is mechanically stabilized by positively anchoring the lead tip so that it remains securely in place during the lifetime of the implant. Current active fixation leads employ helices having lengths in the range of 1.8 to 2.0 mm when fully extended from the lead's distal tip.

The fixation helix may itself function as a tip electrode (typically the cathode) in which case it is conventionally coupled by means of an electrical conductor to a rotatable pin terminal on the connector assembly. Rotational torque applied to the connector pin at the proximal end of the lead is transmitted via the conductor to the helix electrode which is thereby screwed into the endocardium. Removal of the screw-in electrode from the heart tissue is effected by counter rotation of the connector pin. Thus, in a lead having a screw-in helix electrode, the coil conductor is used not only as a conductor for electrically coupling the connector pin with the helix electrode, but also as a tool for extending or retracting the helix electrode relative to the distal end of the lead during lead fixation or removal by rotating the connector pin.

Whether the screw-in helix is electrically active or not, the degree of extension of the helix relative to the lead tip must be verifiable by the implanting physician. The current practice is to employ fluoroscopy as a visual feedback mechanism to ascertain whether the helix is fully extended. In aid of such visual confirmation, a high-density, radiopaque, metal collar is typically incorporated in the distal tip of the lead. The collar thus serves as a fluoroscopic helix extension marker. In addition, the electrical conductivity of the collar allows it to be used to sense electrical signals generated by the cardiac tissue adjacent to the distal tip of the lead. The collar may thereby function as a source electrode for mapping localized heart activity prior to the deployment of the electrically active helix electrode. Thus, such mapping helps find, in a non-traumatic manner, a location for installing the helix electrode to optimize sensing and stimulation thresholds. Where the helix is electrically active so as to serve as an electrode, the helix and mapping collar are typically electrically connected in parallel to collectively function as the cathode.

The visual, fluoroscopic confirmation of helix extension has certain limitations. It neither guarantees (1) that the fully extended length of the helix is embedded in the heart tissue, that is, that no part of the helix remains exposed, nor (2) that the distal end of the lead is perpendicular to the local endocardium, that is, that the lead tip is in full engagement with that tissue. Thus, it would be desirable to eliminate having to rely exclusively on visual, fluoroscopic confirmation. Chronically, with fibrotic growth around an exposed portion of the helix, an implanted lead would be susceptible to both mechanical instabilities (in the form of micro- and macro-dislodgements) and electrical instabilities manifested by sensing amplitude decreases, capture threshold increases, and/or electrode impedance decreases.

Another issue associated with active fixation leads is that different physicians prefer different tip electrode impedances (defined generally as the resistance to current flow from the electrode to the heart tissue). While some physicians prefer impedances in the 500 ohm range others seek impedances greater than 1,000 ohms. However, current technologies limit the impedance values that active fixation leads can provide.

SUMMARY

In accordance with one specific embodiment, there is provided an implantable medical lead comprising a helix electrode extendable and retractable relative to a distal tip of the lead, and an electrically conductive mapping collar disposed at the distal tip. The lead includes a proximal end carrying an electrical connector assembly. The electrical connector assembly comprises a first terminal connected to the helix electrode and a second terminal separately connected to the mapping collar.

A significant advantage of a lead having independent helix electrode and mapping collar circuits is that the implanting physician can confirm from separate electrode impedance readings that the helix is in fact extended and fully embedded within the myocardium. Further, the independent mapping collar and helix electrode circuits may be used, in conjunction with a configurable or programmable switch network, to provide the implanting physician with a choice of electrode impedances.

In accordance with another aspect of the present invention, there is provided a method of determining whether the distal tip of an implantable medical lead is properly positioned relative to body tissue wherein the medical lead comprises an extendable/retractable helix electrode at the distal tip of the lead and an electrically conductive mapping collar disposed at the distal tip. The method comprises (a) with the helix electrode retracted, selecting an implant site along the body tissue using the mapping collar; (b) extending the helix electrode so that it penetrates the body tissue at the selected implant site; (c) measuring an electrical impedance value for the mapping collar; (d) comparing the measured electrical impedance value with a predetermined impedance value for the mapping collar; (e) if the measured electrical impedance value for the mapping collar is below said predetermined value, repositioning the helix electrode relative to the body tissue and repeating at least steps (c)-(e); and (f) if the measured electrical impedance value of the collar is equal to or above said predetermined value, retaining the distal tip of the lead at said selected implant site.

Helix extension may be verified visually, for example, fluoroscopically.

Pursuant to yet another aspect of the invention, there is provided a method of electrically verifying that an extendable/retractable helix electrode at the distal tip of a medical lead is properly positioned relative to the myocardial tissue of a heart, the lead including an electrically conductive mapping collar disposed at said distal tip. The method comprises (a) with the helix electrode retracted, selecting an implant site using the mapping collar; (b) extending the helix electrode so that it penetrates the tissue of the heart at a selected implant site; (c) measuring an electrical impedance value for the helix electrode; (d) comparing the measured electrical impedance value with a predetermined impedance value for the helix electrode; (e) if the measured electrical impedance value for the helix electrode is below said predetermined value, repositioning the helix electrode relative to the heart tissue and repeating at least steps (c)-(e); and (f) if the measured electrical impedance value for the helix electrode is equal to or above said predetermined value, retaining the helix electrode at the selected implant site.

In accordance with yet another aspect of the invention, there is provided a system for providing electrical stimulation to selected cardiac tissue and for sensing electrical signals generated by the tissue. The system comprises an implantable medical lead including a helix electrode extendable and retractable relative to a distal tip of the lead, an electrically conductive mapping collar disposed at the distal tip, and an electrical connector assembly carried by a proximal end of the lead. The electrical connector assembly comprises a first terminal connected to the helix electrode and a second terminal separately connected to the mapping collar.

The system further comprises an IMD including a receptacle for receiving the connector assembly of the medical lead, the receptacle enclosing electrical contacts adapted to be engaged by the terminals on the electrical connector assembly. The IMD further comprises electrical IMD circuitry and a switch network interposed between the IMD circuitry and the receptacle contacts, the switch network being configurable to connect to the ID circuitry the helix electrode only, the collar electrode only, the series combination of the helix electrode and the collar, or the parallel combination of the helix electrode and the collar. In this fashion, a range of electrode impedances is made available to suit the personal preferences of the implanting physician.

BRIEF DESCRIPTION OF THE DRAWINGS

The foregoing and other aspects, features and advantages of the invention will be evident to those skilled in the art from the detailed description below, taken together with the accompanying drawings, in which.

DETAILED DESCRIPTION OF THE INVENTION

The following description is of a best mode presently contemplated for practicing the invention. This description is not to be taken in a limiting sense but is made merely for the purpose of describing the general principles of the invention whose scope may be ascertained by referring to the appended claims.

Figure 1:
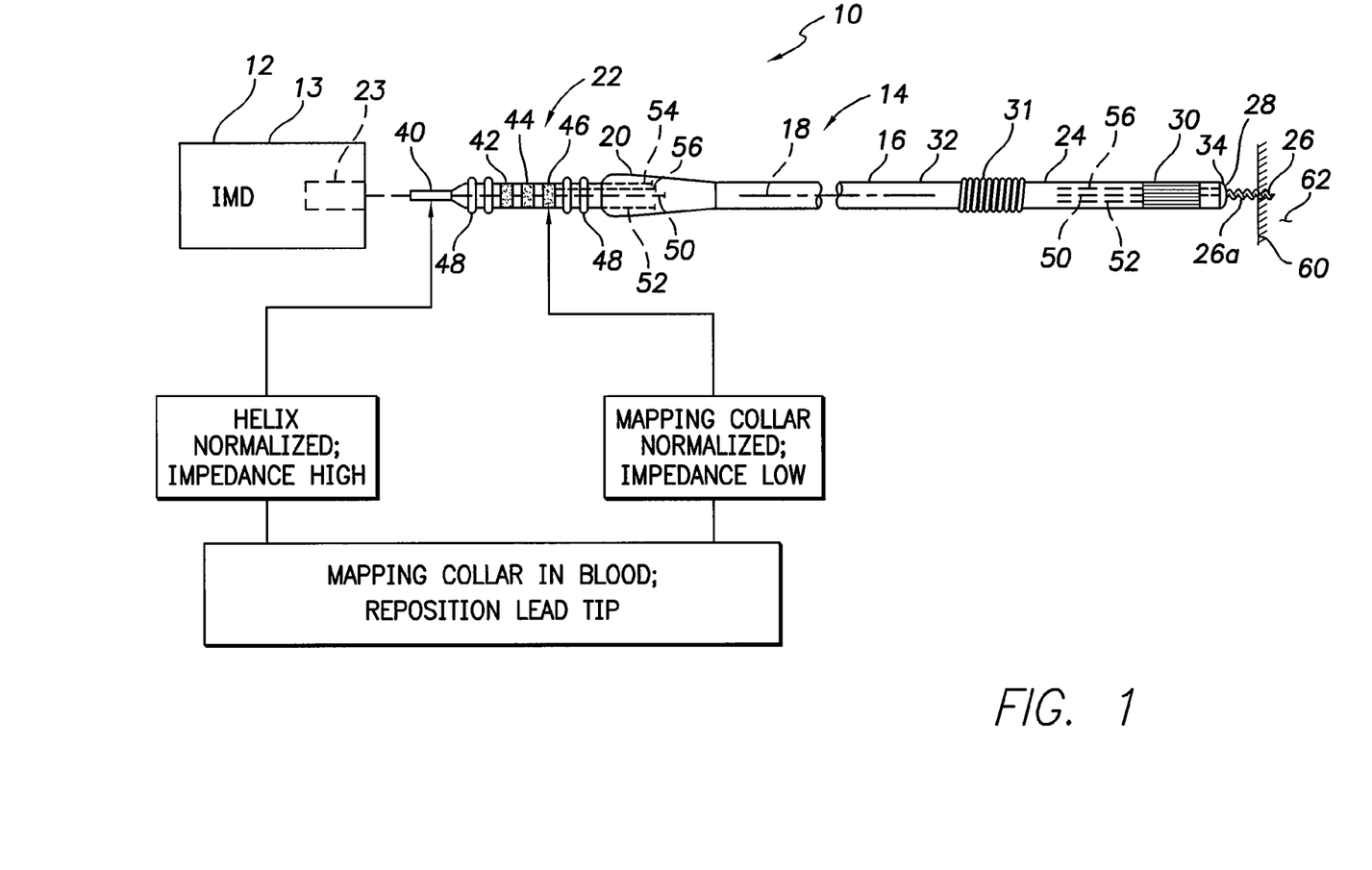
FIG. 1 is a simplified side view of an endocardial, active fixation, bipolar pacing and sensing lead system and impedance measuring means in accordance with one specific, exemplary embodiment of the invention, and wherein the helix electrode of the lead is shown only partially embedded in the myocardium.

With reference to FIG. 1, there is shown an endocardial, bipolar pacing/sensing lead system 10 in accordance with one, specific, exemplary embodiment of the invention. The system comprises an implantable medical device (IMD) 12 such as a cardiac IMD or implantable cardioverter defibrillator (ICD) and an endocardial, bipolar, active fixation cardiac pacing and sensing lead 14 for connecting the IMD 12 with selected cardiac tissue whose electrical activity is to be stimulated and/or sensed. The electrical components of the IMD 12 are hermetically sealed within an electrically conductive, metallic casing or can 13. The lead 14 includes a lead body 16 extending along a central, longitudinal axis 18. The lead body 16 has a proximal end 20 carrying a connector assembly 22 adapted to be received by a receptacle 23 formed in the IMD 12 for electrically connecting the lead body 16 to electrical circuitry within the IMD 12. The lead body 16 further comprises a distal end portion 24, a helical, screw-in fixation element or helix 26 adapted to be extended or retracted relative to a distal tip 28 of the lead body, and a ring electrode 30 carried by the distal end portion 24 proximal of the distal tip 28. The ring electrode 30 typically functions as an anode. The lead body may further carry one or more shocking coils, represented by a single coil 31, for providing cardioverting or defibrillating stimulation. The helix 26 serves to stabilize or anchor the distal end portion 24 of the lead body relative to the tissue and is electrically active so as to also function as an electrode (typically the cathode). When implanted, the helix 26 stimulates selected cardiac tissue such as the tissue of the right ventricle of the heart and/or senses the electrical activity of that tissue. Consistent with teachings well known in the art, one or more portions of such a helix electrode may be electrically insulated along its length.

The lead body 16 is comprises a tubular sheath or housing 32 made of a biocompatible, biostable, electrically insulating material such as silicone rubber, polyurethane or a combination of both. Disposed at the distal tip 28 of the lead body is an electrically conductive mapping collar 34 that may also serve as the cathodal electrode or a portion thereof. The collar 34 typically comprises a high density, biocompatible, biostable, substantially radiopaque metallic material such as platinum, gold or tantalum or an alloy such as platinum/iridium 90/10 or 80/20. The outer surface of the collar 34 may have a permeable or porous texture to increase its effective surface area and to promote rapid tissue ingrowth following implantation. The desired porosity may be provided in various known ways, for example, by sintering platinum particles to the outer surface of the collar 34 or by depositing thereon a coating of titanium nitride (TiN).

The connector assembly 22 carried by the proximal end 20 of the lead body 16 is adapted to electrically and mechanically couple the lead body to the IMD 12. For the example shown, the connector assembly 22 includes coaxial terminals in the form of a tubular, rotatable pin terminal 40 and three ring terminals 42, 44 and 46 positioned to engage corresponding electrical contacts within the receptacle 23 in the IMD 12. To prevent ingress of body fluids into the receptacle, the connector assembly may be provided with spaced-apart sets of seals 48. Further, in accordance with well-known implantation techniques, a stylet or guide wire (not shown) for delivering and steering the distal end portion 24 of the lead body during placement thereof relative to the target tissue may be inserted through the tubular connector pin 40 and into a longitudinal passageway within the lead body housing 32, which passageway may comprise one of the lumens of a multilumen housing. The stylet or guide wire passageway may also comprise the lumen of a coil dedicated for that purpose or also serving as an electrical conductor connecting the pin terminal 40 with the helix electrode 26.

The ring electrode 30 and the shocking coil 31 may be connected to the ring terminals 42 and 44, respectively. Thus, the insulating, tubular sheath 32 encloses three electrical conductors 50, 52 and 54 connecting, respectively, the helix electrode 26 with the rotatable pin terminal 40, the ring electrode 30 with the ring terminal 42, and the shocking coil 31 with the ring terminal 44 on the connector assembly 22.

Figure 2:
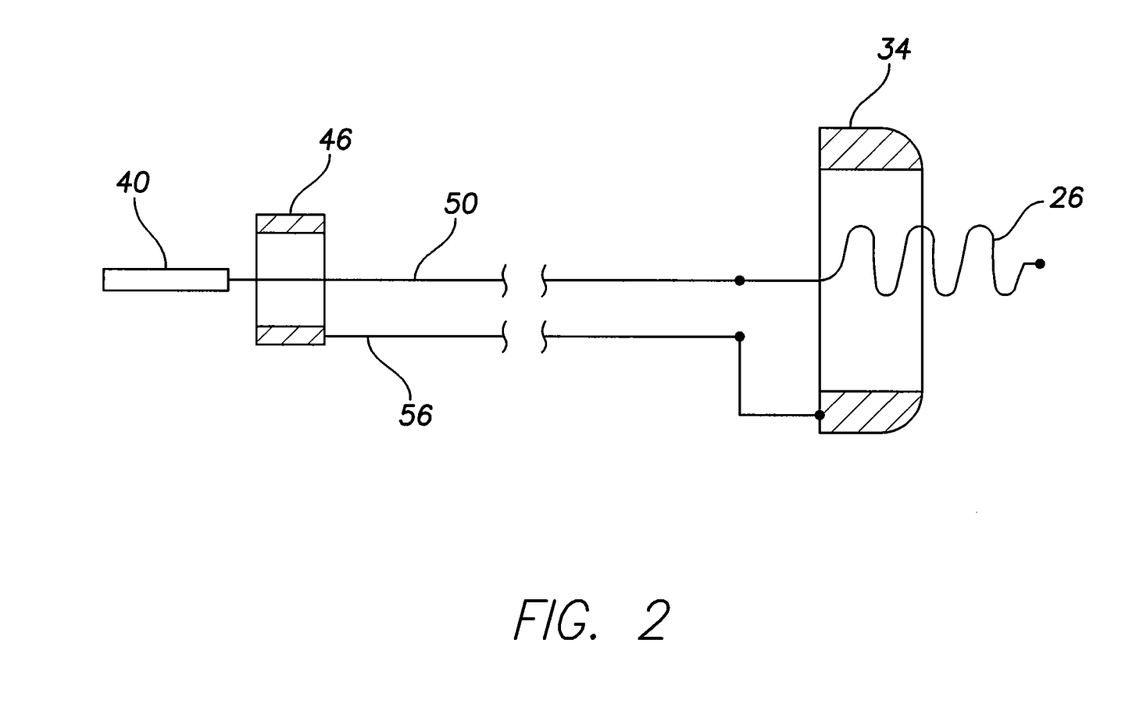
FIG. 2 is a schematic side view, in cross section, of the helix and the mapping collar of the lead of FIG. 1 showing their separate electrical connections with associated terminals on the electrical connector assembly of the lead, in accordance with a preferred form of the invention.

With reference now also to FIG. 2, in accordance with an aspect of the invention, the helix 26 is connected to the pin terminal 40 by a conductor 50 and the mapping collar 34 is separately connected to the ring terminal 46 by an electrical conductor 56. Thus, unlike the parallel connection of the helix and mapping collar to a single terminal on the connector assembly as in the prior art, in the present invention the helix 26 and the collar 34 are independently connected to separate, respective terminals 40 and 46.

Referring again to FIG. 1, the helix electrode 26, although perpendicular to the endocardium 60, is depicted as only partially embedded in the myocardium 62, so that a proximal portion 26a of the helix is exposed to body fluid, chiefly blood, within the heart. Since the electrical resistivity of blood is less than that of body tissue, the implanting physician can ascertain, using an instrument such as a Pacing System Analyzer (PSA), whether the collar 34 is in contact with the endocardium 60. In the example shown in FIG. 1, with the helix electrode 26 only partially embedded in the myocardium, the PSA will display a low collar impedance indicating that the mapping collar is immersed in blood and that the lead tip 28 should be repositioned.

Figure 3:
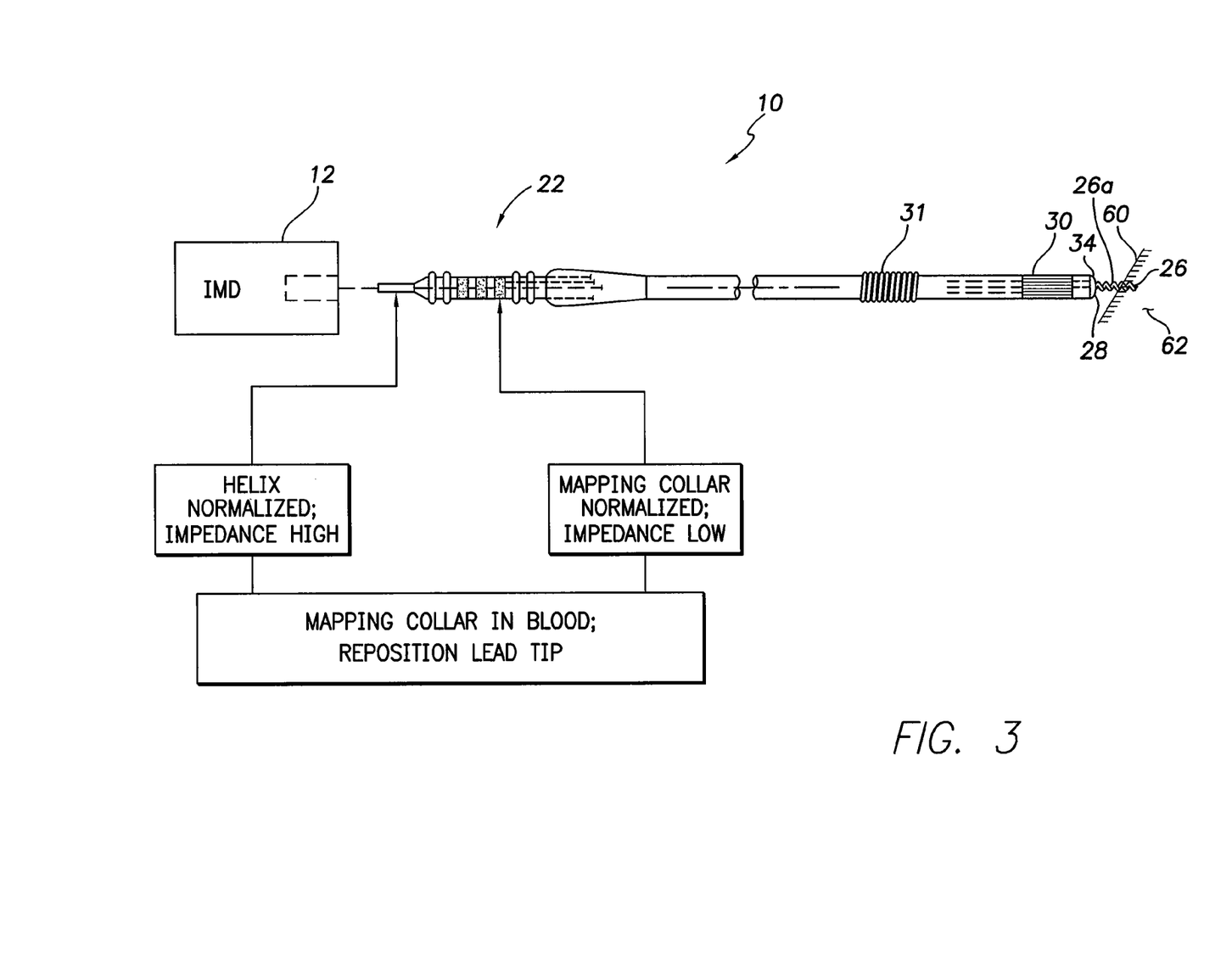
FIG. 3 is a simplified side view of the lead system of FIG. 1 in which the helix electrode of the lead is embedded only partially in the myocardium and oriented at a non-perpendicular angle relative to the endocardium.

FIG. 3 shows another possible undesirable orientation of the helix electrode 26 and collar 34 relative to the endocardium 60. Here, not only is a portion 26a of the helix 26 exposed to blood, but the helix is also not perpendicular to the endocardium 60. Thus, like the case depicted in FIG. 1, although the helix electrode impedance measures high, the collar impedance will again measure low indicating that the lead tip 28 should be repositioned.

Figure 4:
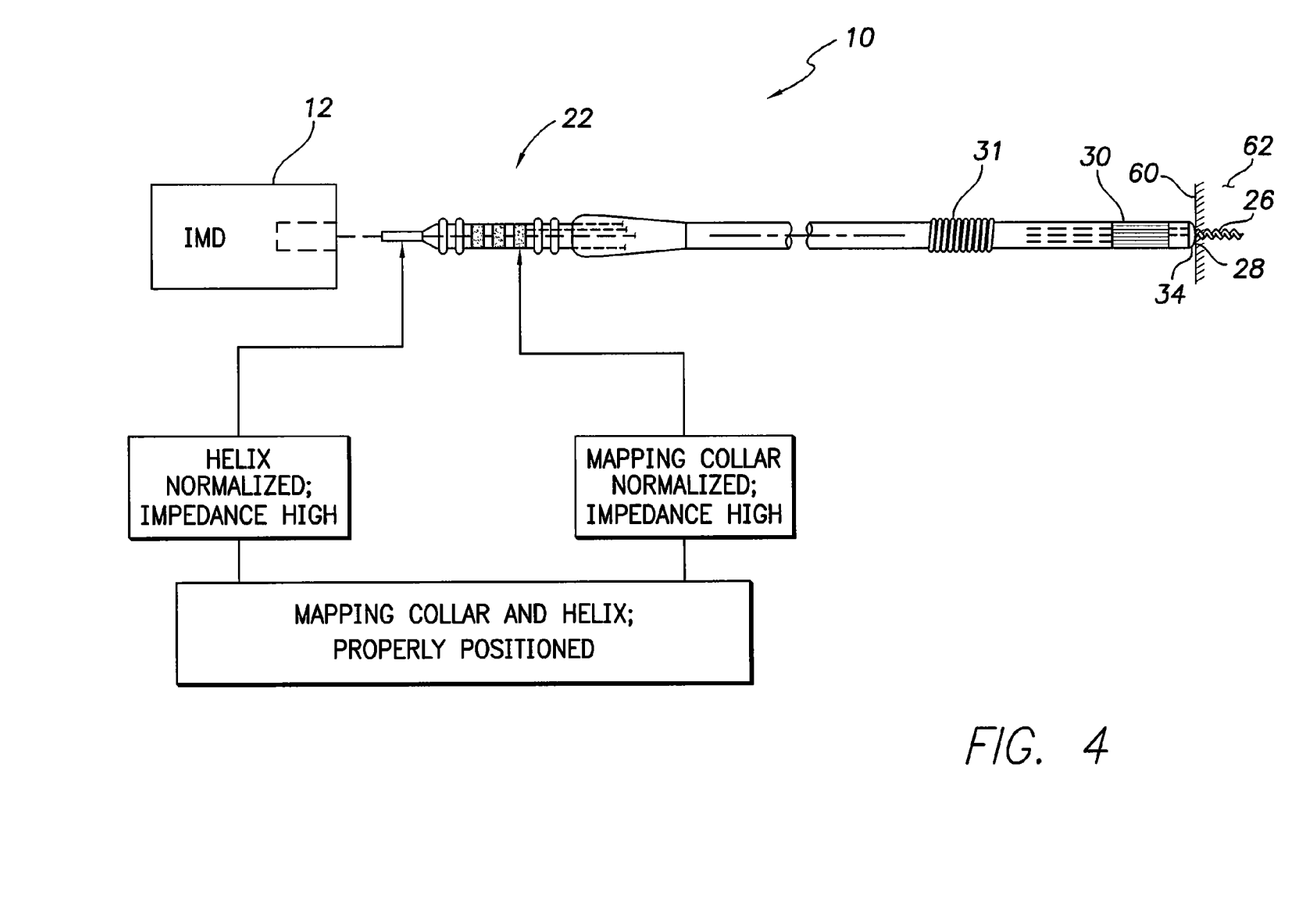
FIG. 4 is a simplified side view of the lead system of FIG. 1 in which the helix electrode of the lead is fully embedded within the myocardium and the lead tip is in full engagement with the surface of the endocardium.

FIG. 4 depicts the case in which the lead tip 28 is properly positioned. Specifically, the helix electrode 26 is shown fully embedded within the myocardium 62 and perpendicular to the endocardium 60, with the collar 34 in full engagement with the endocardium 60. In this case, the measurements of both helix and collar impedances will be high and the proper positioning of these elements may be assumed. Helix extension verification may, of course, be effected fluoroscopically.

In accordance with another aspect of the present invention, there is provided a method of electrically determining whether the distal tip of an implantable medical lead such as that shown in FIG. 1 is properly positioned relative to body tissue. The medical lead comprises an extendable/retractable helix electrode at the distal tip of the lead and an electrically conductive mapping collar disposed at the distal tip. An embodiment of the method is illustrated in the flow chart of FIG. 5. In step 80, an implant site is selected along the body tissue using the mapping collar with the helix electrode retracted. In step 82, the helix electrode is extended so that it penetrates the body tissue at the implant site. In step 84, an electrical impedance value, $Z_C$, for the mapping collar is measured, and a predetermined or reference collar impedance, $Z_{CREF}$, for example, 100 ohms/mm$^2$, is obtained or retrieved in step 86. The measured and reference impedance values are preferably normalized to account for differing surface areas.

Figure 5:
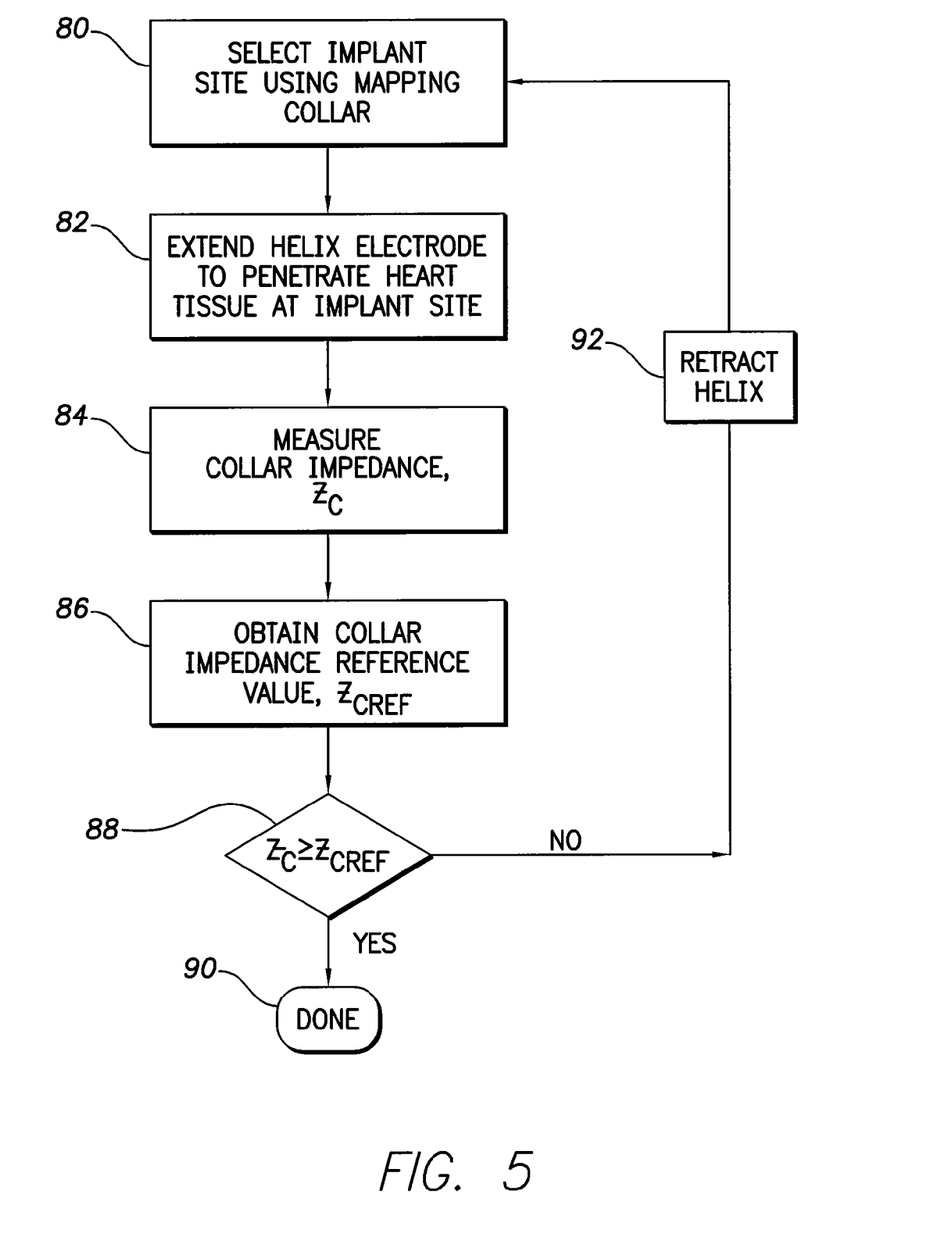
FIG. 5 is a flow chart illustrating an exemplary embodiment of a method for electrically determining in vivo whether a lead such as that shown in FIG. 1 has been properly positioned relative to body tissue such as the endocardium.

Next, in a decision step 88, a comparison is made between the measured and reference impedance values. If the measured electrical impedance value of the collar is equal to or above the predetermined electrical impedance value, the process is ended at step 90 and the distal tip of the lead is maintained at the selected implant site. If the measured impedance is below the predetermined value, the helix electrode is repositioned. Repositioning of the helix electrode may simply involve screwing the helix electrode further into the tissue and then rechecking the impedance. Alternatively, by way of step 92, the helix electrode may be retracted and the steps 80 through 88 repeated. Helix extension may be verified visually, for example, fluoroscopically.

Figure 6:
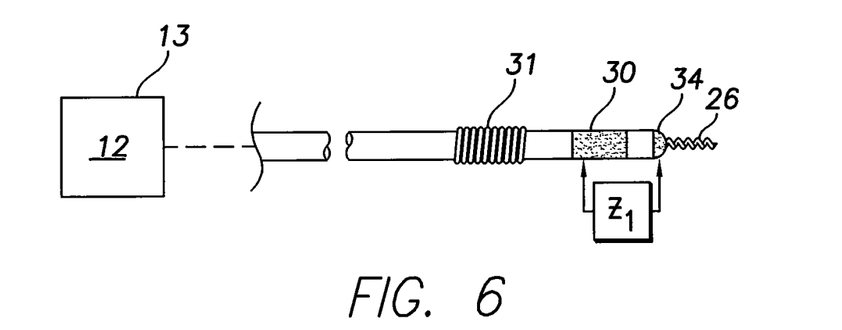
FIGS. 6, 7 and 8 are simplified side views of the distal end portion of the lead of FIG. 1 showing collar impedance measurements made, respectively, collar-to-ring electrode, collar-to-shocking electrode, and collar-to-IMD casing.
Figure 7:
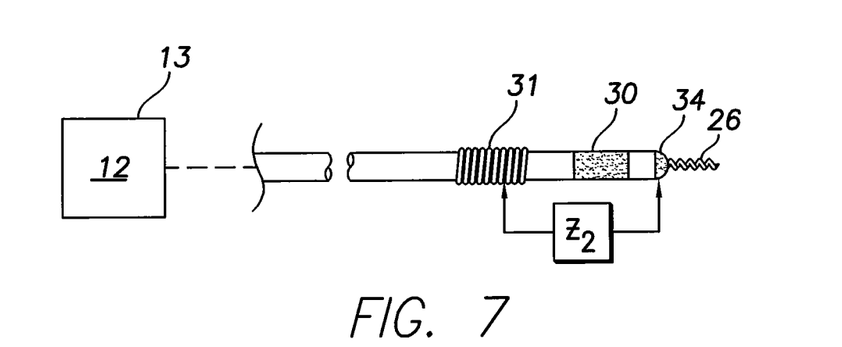
Figure 8:
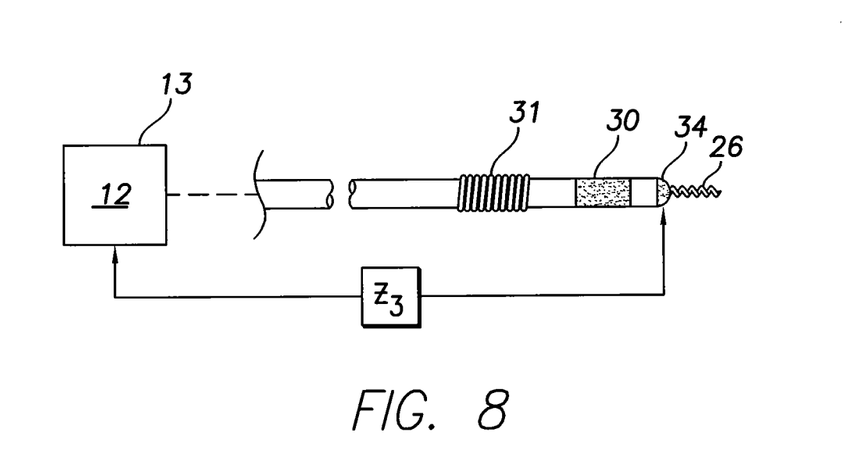

As shown in FIGS. 6-8, collar impedance may be measured in various ways: relative to the ring electrode 30 (impedance $Z_1$) (FIG. 6), the shocking coil 31 (impedance $Z_2$) (FIG. 7), or the IMD casing or can 13 (impedance $Z_3$) (FIG. 8). These impedance measurements are preferably normalized to account for differing surface areas and expressed in terms of, for example, ohms/mm$^2$.

Figure 9:
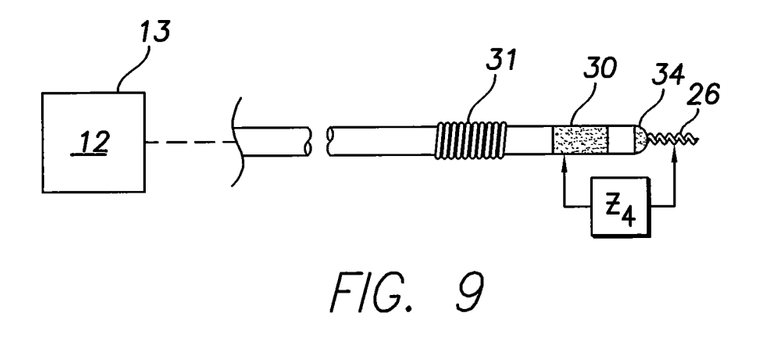
FIGS. 9, 10 and 11 are simplified side views of the distal end portion of the lead of FIG. 1 showing helix electrode impedance measurements made, respectively, helix-to-ring electrode, helix-to-shocking electrode, and helix-to-IMD casing.
Figure 10:
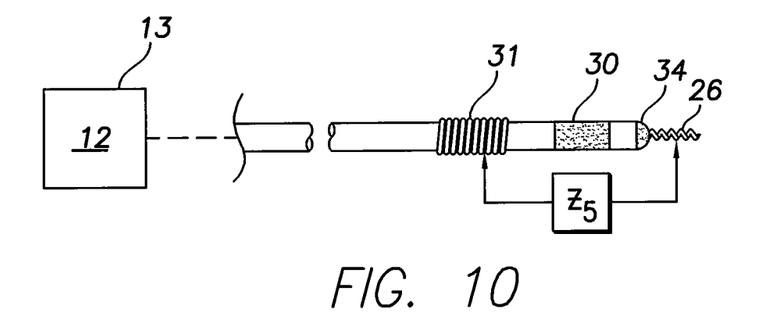
Figure 11:
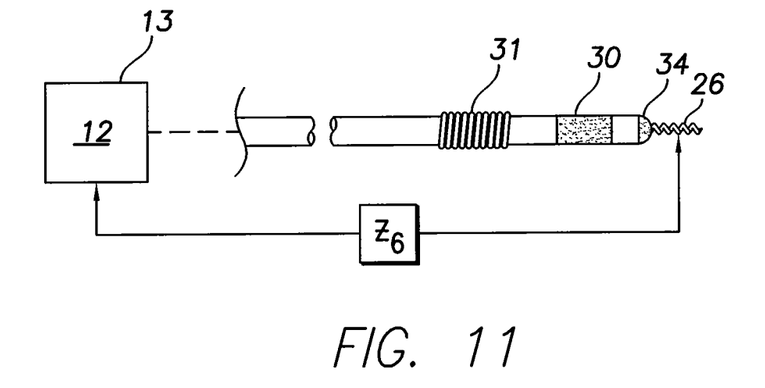

Proper placement of the helix electrode 26 may be independently verified electrically by measuring helix electrode impedance using, for example, a PSA, along the lines employed for measurement of collar impedance and comparing the measured helix electrode impedance with a predetermined or reference value thereof. As with the collar electrode, helix electrode impedance may be measured relative to the ring electrode 30 (impedance $Z_4$) (FIG. 9), the shocking coil 31 (impedance $Z_5$) (FIG. 10), or the IMD case or can 13 (impedance $Z_6$) (FIG. 11).

Collar and helix electrode impedance trends may be ascertained by storing initial or reference values of the collar and helix impedances and then periodically measuring the impedances and comparing those periodic measurements with the stored values.

Figure 12:
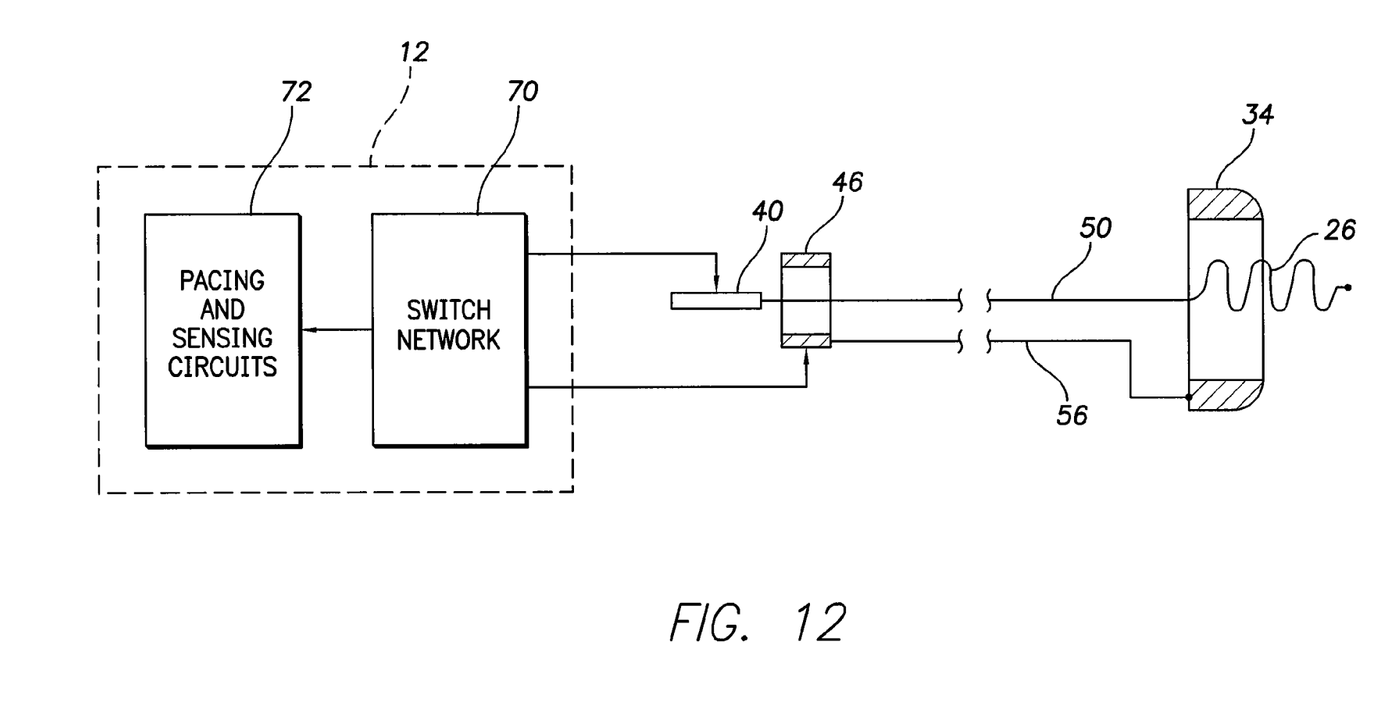
FIG. 12 is a schematic side view along the lines of FIG. 2 in accordance with an alternative embodiment of the invention that includes a switch network permitting selection of various cathodal impedances.

The independent electrical connections of the helix 26 and collar 34 provides yet another benefit, namely, a range of electrode impedances may be made available to suit the preferences of different lead-implanting physicians. With reference to FIG. 12, the circuitry within the IMD 12 may include a switch network 70 electrically coupled to the helix pin terminal 40 and the collar ring terminal 46. The switch network 70 may be programmed or otherwise configured by the implanting physician to connect various electrical combinations of the helix 26 and collar 34 to the IMD pacing and sensing circuitry 72, namely, helix only, collar only, the series combination of the helix and collar, and the parallel combination of the helix and collar. These combinations will typically provide a choice of electrode impedances in the range of 500 to 1200 ohms. It will be evident that as an alternative, the switch network may be incorporated within the lead itself.

While several illustrative embodiments of the invention have been disclosed herein, still further variations and alternative embodiments will occur to those skilled in the art. Such variations and alternative embodiments are contemplated, and can be made without departing from the spirit and scope of the invention as defined in the appended claims.

What is claimed is:

1. A system for providing electrical stimulation to cardiac tissue and for sensing electrical signals generated by said tissue, the system comprising:
   an implantable medical lead comprising:
      a helix electrode extendable and retractable relative to a distal tip of the lead;
      an electrically conductive mapping collar disposed at said distal tip; and
      an electrical connector assembly carried by a proximal end of the lead, the electrical connector assembly comprising a first terminal connected to the helix electrode and a second terminal separately connected to the mapping collar; and
   an IMD comprising:
      a receptacle for receiving the connector assembly of the medical lead, the receptacle enclosing electrical contacts adapted to be engaged by the terminals on the electrical connector assembly;
      electrical IMD circuitry; and
      a switch network interposed between said IMD circuitry and said receptacle contacts, said switch network being configurable to connect to the electrical IMD circuitry the helix electrode only, the collar electrode only, the series combination of the helix electrode and collar, or the parallel combination of the helix electrode and collar, whereby a range of electrode impedances is made available.

2. The system of claim 1 wherein the lead further comprises a ring electrode and wherein the impedance value is measured between the collar and the ring electrode.

3. The system of claim 1 wherein the lead further comprises a shocking electrode and wherein the pacing impedance value is measured between the collar and the shocking electrode.

4. The system of claim 1 wherein the lead further comprises a proximal end carrying an electrical connector assembly adapted to be received by an implantable medical device having an electrically conductive case, and wherein said impedance value is measured between said collar and said case.

5. The system of claim 1 wherein the implantable medical device further comprises means for electrically verifying whether said helix electrode is properly positioned relative to the myocardium.

* * * * *